United States Patent [19]

Annis et al.

[11] Patent Number: 4,839,913
[45] Date of Patent: Jun. 13, 1989

[54] SHADOWGRAPH IMAGING USING SCATTER AND FLUORESCENCE

[75] Inventors: Martin Annis, Cambridge; Paul Bjorkholm, Sharon, both of Mass.

[73] Assignee: American Science and Engineering, Inc., Cambridge, Mass.

[21] Appl. No.: 40,018

[22] Filed: Apr. 20, 1987

[51] Int. Cl.$^4$ .............................................. G21K 5/10
[52] U.S. Cl. ...................................... 378/44; 378/87; 378/99; 378/146
[58] Field of Search .................. 378/44, 45, 46, 57, 378/98, 99, 6, 87, 146

[56] References Cited

U.S. PATENT DOCUMENTS

| | | | |
|---|---|---|---|
| 28,544 | 9/1975 | Stein et al. | 250/369 |
| 2,670,401 | 2/1954 | Weinberg | 378/87 |
| 2,730,566 | 1/1956 | Bartow et al. | 378/44 |
| 3,106,640 | 10/1963 | Oldendorf | 250/52 |
| 3,114,832 | 12/1963 | Alvarez | 250/51.5 |
| 3,525,863 | 8/1970 | Constantine et al. | 250/51.5 |
| 3,769,507 | 10/1973 | Kenney et al. | 250/52 |
| 3,778,614 | 12/1973 | Hounsfield | 250/362 |
| 3,866,047 | 2/1975 | Hounsfield | 250/360 |
| 3,881,110 | 4/1975 | Hounsfield et al. | 250/360 |
| 3,927,318 | 12/1975 | Macovski | 378/44 |
| 3,940,625 | 2/1976 | Hounsfield | 250/360 |
| 3,944,833 | 3/1976 | Hounsfield | 250/367 |
| 3,946,234 | 3/1976 | Hounsfield | 250/363 S |
| 4,031,545 | 6/1977 | Stein et al. | 358/108 |
| 4,104,519 | 8/1978 | Oldendorf | 378/44 |
| 4,179,100 | 12/1979 | Sashin et al. | 378/44 |
| 4,251,726 | 2/1981 | Alvarez | 250/302 |
| 4,350,889 | 9/1982 | Lisnyansky | 378/46 |
| 4,357,535 | 11/1982 | Haas | 378/57 |
| 4,510,573 | 4/1985 | Boyce et al. | 364/498 |
| 4,618,773 | 10/1986 | Drukier | 250/363 S |

OTHER PUBLICATIONS

Sellers et al, "Signature Comparison Technique for Rapid Alloy Sorting with a Radioisotope Excited X-Ray Analyzer", *Materials Research and Standards*, vol. 10, No. 11, Nov. 1970, pp. 16-18.

Hoffer, "Fluorescent Thyroid Scanning", The American Journal of Roentgenology, vol. 105, No. 4, Apr. 1969, pp. 721-727.

Hoffer et al, "Fluorescent Thyroid Scanning: Scanning without Radioisotopes", Radiology, vol. 99, Apr.-Jun. 1971, pp. 117-123.

Stein et al, "Flying Spot X-Ray Imaging Systems", Materials Evaluation, vol. XXX, No. 7, Jul. 1972, pp. 137-148.

*Primary Examiner*—Craig E. Church
*Attorney, Agent, or Firm*—Pollock, Vande Sande & Priddy

[57] ABSTRACT

Information is derived from a selected fluorescent radiation line produced when an object is illuminated by a flying spot scanner. The illuminating radiation has an energy level sufficient to produce the fluorescent line when targeted components of the object are present and illuminated. A detector senses a fluorescent radiation line emitted from the targeted components to generate electrical fluorence based signals.

43 Claims, 3 Drawing Sheets

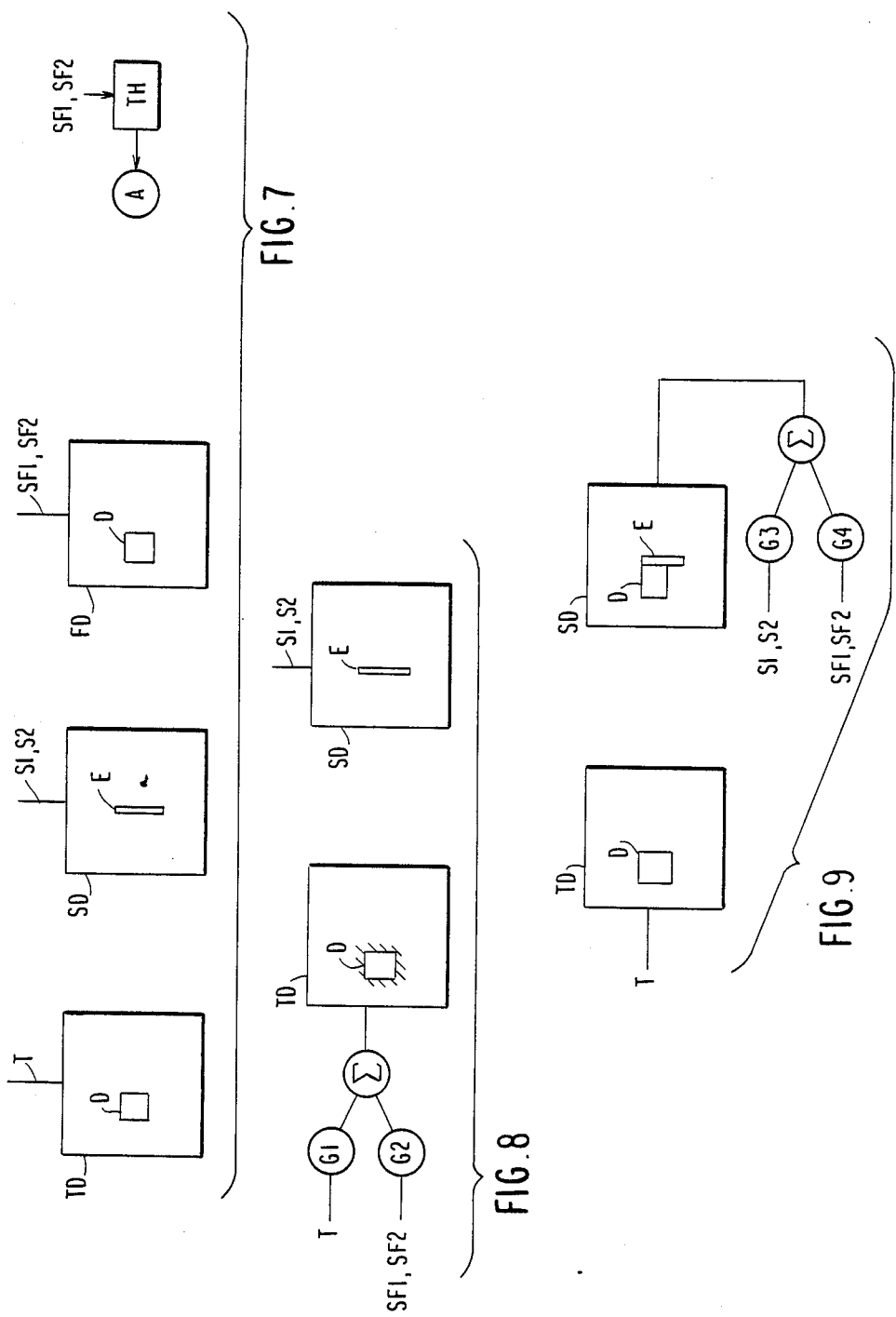

SHADOWGRAPH IMAGING USING SCATTER AND FLUORESCENCE

DESCRIPTION

1. Technical Field

The present invention relates to improvements in imaging in general, and in particular improvements relying on detecting fluorescent radiation.

2. Related Application

This application is related to our copending application Ser. No. 876,632 filed June 20, 1986, the disclosure of which is incorporated herein by this reference.

2. Background Art

X-ray imaging is a technique which has been applied for many years in both the medical field as well as in non-destructive testing. X-ray images are developed in general by illuminating an object, detecting the resulting radiation and using the resulting radiation to develop an image. More recently, an intermediate step of converting the radiation to electrical signals has been interposed; this allows tailoring the image by processing the electrical signals. For purposes of the present invention, we can divide the entire field of X-ray imaging to what we will refer to as either shadowgraph imaging or composite imaging. Rather than attempting to define these terms, they will be defined by example.

Shadowgraph imaging was initially employed by flooding the object to be imaged with illuminating radiation so that as a function of both time and space, the radiation was two valued, absent or present, and where present the radiation was at least relatively uniformly spatially distributed. The radiation transmitted through or scattered from the ogject was recorded, typically on photographic film and the image which was produced was in the nature of a shadowgraph in that each point in the image represented the line of sight transmissivity of the object which had been illuminated. At least two defects are recognized in such a shadowgraph image. In the first place, the intensity of the energy recorded for any point represented a line of sight integral of absorption between the recording plane and the illuminating point. There is no way to tell, from the resulting image, whether the absorption was uniformly distributed across the line of sight or instead was relatively concentrated. Further reducing the effectiveness of such a shadowgraph image is the fact that through mechanisms such as scattering and fluorescence, components of the object in one line of sight could contaminate that point of the image recorded for another line of sight. Nevertheless, useful information could be extracted from such a shadowgraph; one example of a shadowgraph which is still in use today is the typical medical x-ray.

An improvement in shadowgraph imaging was the use of the flying spot scanner, described in Stein et al Reissue Patent No. 28,544 and the Stein et al publication "Flying Spot X-ray Imaging Systems" appearing in *Materials Evaluation*, Vol. XXX, No. 7, July 1972 at pages 137–148. While the flying spot scanner did not eliminate the first problem of shadowgraphs mentioned above, it did go a long way toward reducing or eliminating the second problem.

Composite imaging differs from shadowgraph imaging in that while we may record the absorption along the plurality of different lines of sight between an x-ray source and a recording plane, we do not use that information, alone, to produce our image. Rather, we mix the information from a plurality of lines of sight in order to produce the resulting image. Examples of this type of imaging are referred to as planar laminography, see Olendorf No. 3,106,640 or other related techniques. Another very popular technique is computed tomography, see Hounsfield Nos. 3,778,614; 3,866,047; 3,881,110; 3,940,625; 3,944,833 and 3,946,234 as examples.

In many embodiments of both shadowgraph imaging and composite imaging, the information forming the image is derived from the variation in intensity of the transmitted energy occasioned by its passage through the object which is illuminated; this is sometimes referred to as a transmitted image. A more recent improvement in shadowgraph imaging is described in our copending patent application Ser. No. 876,632 filed June 20, 1986. That application describes apparatus which extracts additional information from the object being illuminated by developing an image from scattered x-ray energy; this is sometimes referred to as a scattered image. As described in the referenced application, scattering preferentially occurs from low atomic number components of the object. Accordingly, as described in the application, at least two images are developed, one may be a transmitted image and another is a scattered image; the former image provides evidence of medium or high atomic number components whereas the scatter image provides evidence of low atomic number components.

Fluorescence is another phenomenon (which is not restricted to x-ray analysis); in the x-ray field it is produced as a result of the photo-electric effect. The photo-electric effect is evidenced when an x-ray photon is totally absorbed by an atom with the simultaneous emission of a bound electron. The x-ray photon disappears and the energy of the x-ray photon is divided between the excitation energy of the atom and the kinetic energy of the emitted electron. The excited atom may quickly emit a subsequent x-ray photon, characteristic of the particular atom. While the use of fluorescence is reported in prior art x-ray analysis systems, see Alvarez Patent No. 3,114,832l; Constantine et al Patent No. 3,525,863; Alvarez Patent No. 4,251,726 and Lisnyansky Patent No. 4,350,889; these prior art examples are not imaging systems. Rather, they attempt to infer or measure the proportion of certain components in a complex object, by measuring the fluorescence energy emitted from the object under specified conditions of illumination. Hoffer, in "Fluorescent Thyroid Scanning: Scanning Without Radioisotopes", appearing in *Radiology*, Vol. 99, April 1971 at pages 117 et seq and "Fluorescent Thyroid Scanning" in *The American Journal of Roentgenology*, Vol. 105, Janunary 1969 at pp. 721 et seq, describes production of a fluorescent thyroid scan. The authors describe a source/detector arrangement in which gamma rays are emitted from a source toward the patient's thyroid gland, and the intensity of a selected fluorescent radiation line produced as a result of the illumination is detected. The source/detector is moved over the gland in a rectilinear pattern and the resulting signals are used to form an image. Macovski Patent No. 3,927,318 is an imaging system based on measuring fluorescence, but Macovski relies on computed tomography techniques and is therefore an example of a composite imaging system as opposed to a shadowgraph imaging system.

Although the illumination that has been referred to is x-rays, those skilled in the art are aware that similar results can be produced with other forms of illumination, i.e. gamma rays, etc.

It is an object of the present invention to improve shadowgraph imaging systems by employing information detected from fluorescence of illuminated objects.

SUMMARY OF THE INVENTION

The invention meets these and other objects by attempting to extract more information from radiation emitted by an object illuminated by x-ray or similar energy, than has been employed in the prior art. More particularly, the invention meets these and other objects by deriving information from a selected fluorescent radiation line which is produced when the object is illuminated by a flying spot scanner. The illuminating radiation is selected in energy level so as to be sufficient to produce the fluorescent line when targeted components of the object are present and illuminated. As in other flying spot systems, there is relative motion between the object being illuminated and the source. A radiation detector is located to be responsive to a predetermined fluorescent radiation line emitted from targeted components of the object for generating electrical signals; these are sometimes referred to as fluorescence based signals.

The electrical signals generated in response to detection of a predetermined fluorescent radiation line can be used in one of three ways. In accordance with one embodiment of the invention, those signals are used to drive a display to develop a shadowgraph image of the targeted components of the object emitting the fluorescent radiation line. In other embodiments of the invention, the electrical signals generated by detection of the predetermined fluorescent radiation line can be used to energize an alarm and/or highlight portions of other images such as an image produced from transmitted radiation and/or an image produced by scattered radiation.

In accordance with the invention, an imaging system such as one of the imaging systems described in the above-reference application is enhanced by the addition of an added radiation detector which is arranged to be responsive to a predetermined fluorescent radiation line emitted from targeted components of the object.

In a system as is described in the co-pending application, two (or three) images may be developed of the set of three possible images, including transmitted, back scattered and forward scattered. The signals from the enhancement (the added detector) can be used to generate an additional image, highlight portions of one or more of the pre-existing images or to energize an alarm.

The energy of a fluorescent radiation line emitted by an atom increases with the square of atomic number. For mid-range atomic number atoms such as iron, the emitted x-ray energy is 5 to 15 kilovolts and is typically inadequate to escape from the object (and hence such x-rays will not be detected). On the other hand, for atoms of iodine or those of adjacent atomic number, the predetermined fluorescent radiation line is on the order of 30 kilovolts, and it increases up to about 70 to 80 kilovolts for materials with atomic number near mercury; such fluorescent radiation will typically escape from an object and is therefore capable of being detected. Inasmuch as each atom emits a fluorescent radiation line which is unique to its atomic number, a detector sensitive to a predetermined fluorescent radiation line may be used to discriminate between atoms.

As a concrete example, consider the airport security field in which hand baggage or the like is scanned. An object which would be of great interest to a security officer would be an explosive device including a detonator. Detonators are typically constructed of mercury fulminate or lead azide. With standard baggage inspection systems and/or with the system described in our co-pending application, the detonator (as a high Z component) will appear in the transmitted image only. However, if such a system is enhanced in accordance with the invention, the detonator will appear bright in a fluorescent image (if present) and dark in the transmitted image.

The key to efficient threat detection is tailoring the detection system to the particular radiation signature of the thread being sought. For example, a bomb would not only include the explosive detonator, but the explosive as well. This composite target is typically composed of low atomic number material (the explosive) and high atomic number material (the detonator) in relatively close association. Because of the characteristics of a shadowgraph image, the detonator outline could be masked by another, high atomic number component and in such case, even using the system described in our co-pending application, the images would not call attention to the potential presence of an explosive device. In accordance with one embodiment of this invention, signals from the added detector (arranged to detect a predetermined fluorescent radiation line) generate a third image, a fluorescent image. In that case, the operator could readily mentally associate the bright position in the fluorescent radiation image (reflecting possible presence of a detonator) with that of the bright portion low Z scatter image suggesting the presence of explosive material; the presence of both would be indicative of an explosive device.

Thus the present invention adds the capability of a fluorescent based signal to the transmit and scattered signals of our co-pending application. Because of the flying spot illumination, all signals are synchronous with respect to the target. In other words, at any instant each signal represents a characteristic of a single line of sight (that which is illuminated by the scanner at the particular instant). As a result, while we could develop one, two or three separate images from the three signals, we could also mix two signals (with selected relative gain) so that one signal (the fluorescent based signal, for example) is used to highlight selected regions of an image developed by another signal (such as the transmitted signal). Because of the synchronous nature of the signals, the highlighted image meaningfully represents the illuminated target.

In line with this description, we can use information from the added detector to highlight the transmitted image so the operator would have evidence of the low Z material (in the scatter image) and the fluorescent highlighted portion of the transmitted image to again provide evidence of an explosive device. Note here with proper selection of the predetermined fluorescent line, masking by other high atomic number components is defeated. As a further alternative, the signal from the added detector could be used to activate an audible or visual alarm which, in conjunction with the evidence from the scatter detector (of a low Z material), could also be employed by an operator to evidence the potential for an explosive device in the object being scanned.

There are a variety of radiation detectors which are available. Generally, these detectors have a response characteristic (as a function of impinging energy) which is in the form of a relatively broad high pass filter, e.g. energy above some low threshold and below a much higher threshold will be detected. While this characteristic fits well with the required characteristics for the transmitted energy detector and the scatter energy detector, it does not fit well with the detector whose function is to detect a predetermined fluorescent radiation line. Such a detector is arranged out of the direct path of the illuminting beam, so it is not subject to spurious signals caused directly by the illuminating beam. However, illumination of a complex object also produces scatter, and the scatter comes off at a wide array of angles. Typically, the scatter is relatively low energy, although not necessarily so. In order to prevent scattered energy from being detected by the additional detector, the characteristics of the additional detector are arranged to reject scattered energy. There are a variety of techniques that can be used to effect this filtering function. Generally, the filtering can be implemented by filtering the fluorescence photons before they reach the detector, or by using pulse height discriminators to filter the electrical signals emitted by the detector.

Accordingly, in one aspect, the invention provides a shadowgraph type image which is based on a fluorescent signal, e.g. one produced by a predetermined fluorescent radiation line emitted from targeted components of the object. In accordance with this aspect, the invention provides apparatus useful in imaging for inspecting objects to highlight targeted components of selected radiation signatures comprising:

(a) a source of penetrating radiation selected to produce fluorescence from targeted components of said object,
(b) means for forming radiation emitted by said source into a beam of predetermined cross-section and for repeatedly sweeping said beam across a line in space,
(c) means providing relative motion between said object to be imaged and said line in space,
(d) radiation detector means responsive to a predetermined fluorescent radiation line emitted from said targeted components of said object for generating electrical signals, and
(e) display means responsive to said electrical signals to develop a shadowgraph image of said targeted components of said object emitting said fluorescent radiation line.

This basic fluorescent signal based shadowgraph imaging system can be enhanced by providing a detector for a transmitted ray and additional apparatus to develop a transmitted or projection radiograph therefrom. Apparatus can be employed, driven by the fluorescence based signal to highlight portions of the projection radiograph image. In lieu of or in addition to highlighting portions of the projection radiograph image, an alarm can be energized in response to presence of the fluorescence based electrical signals.

As an alternative, or in addition to apparatus for developing a projection image, a further detector can be provided which responds to scattered radiation. A shadowgraph type image can also be developed based on scatter signals, e.g. signals produced by the scatter detector. Portions of the scatter image can be highlighted if desired based on the fluorescence based signals. The scatter image can be either a forward scatter (based on a detector located further from the source than the object) or a backscatter (based on a detector located closer to the source than the object).

In an alternative arrangement while fluorescence based signals are developed, a fluorescence based image is not developed. In this arrangement, an image is developed by a detector which is responsive to energy emitted by the object, e.g. the detector may be a transmitted (or projection) radiograph detector or a scatter detector. Signals from the detector are used to develop a shadowgraph image (either a projection radiograph or a scatter image). The fluorescence based signals can then be used to highlight portions of the projection or scatter image. An alarm may be provided either alternative to the highlighting apparatus or in addition thereto, energized on the presence of the fluorescence based signals. If a scatter image is developed, that scatter image can be due to either or both of forward or back scatter.

BRIEF DESCRIPTION OF THE DRAWINGS

The present invention will be described in further detail in the following portions of this specification when taken in conjunction with the attached drawings in which like reference characters identify identical apparatus and in which:

FIG. 5 also illustrates a different embodiment of the invention similar to that just described except that the fluorescent detector elements comprise elements 81 and 82 and the scatter detector elements comprise elements 41 and 42;

FIG. 7 illustrates the output in accordance with one embodiment of the invention which comprises a transmit display TD, a scatter display SD, a fluorescent display FD and an alarm A;

FIG. 8 illustrates the output of a different embodiment of the invention, which employs a scatter display SD similar to that shown in FIG. 7 and a transmit display TD in which the transmitted image is highlighted by the fluorescence based signals; FIG. 9 shows the output of still another embodiment of the invention which includes a transmit display TD similar to that shown in FIG. 7 and a scatter display SC in which the scatter image is highlighted based on fluorescence signals.

DETAILED DESCRIPTION OF PREFERRED EMBODIMENTS

Figure 1:
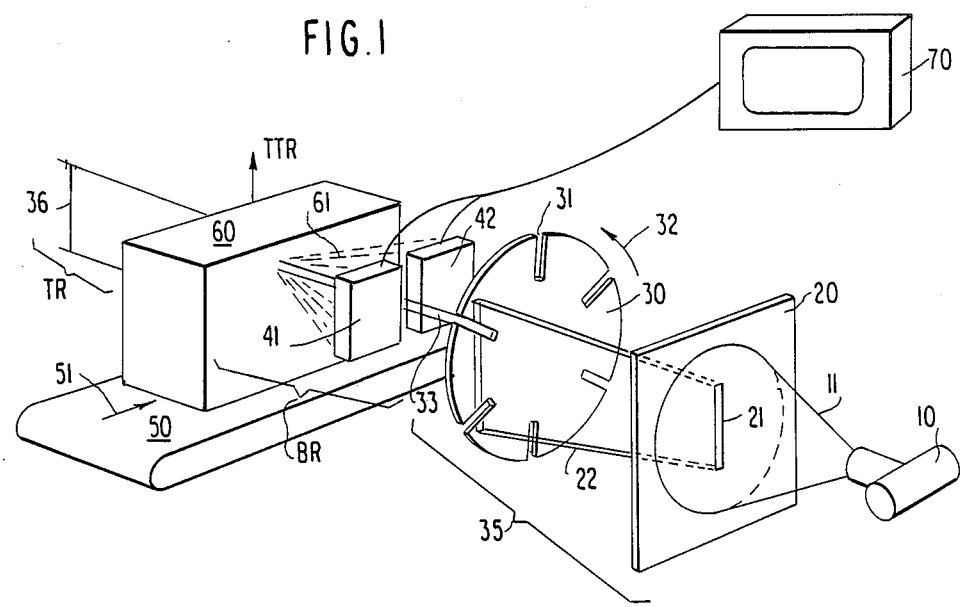
FIG. 1 schematically illustrates an embodiment of the invention wherein an object 60 is illuminated by a flying spot of penetrating radiant energy, and a predetermined fluorescent radiation line emitted from the object 60 is detected and employed to produce a fluorescence based image on the display 70.

In as much as all of the embodiments of the invention are based on deriving what has been termed fluorescence based signals, the apparatus for developing that information will be described in connection with FIG. 1. FIG. 1 shows a system which can not only develop fluorescence based shadowgraph image signals but which will also produce an image therefrom although production of a fluorescence based image is not an essential component of every embodiment of the invention. FIG. 1 shows a source of penetrating radiant energy such as an x-ray source 10 emitting a cone of energy 11 which impinges on a penetrating radiant energy opaque plate 20 with a slit 21 therein. The plate 20 emits a truncated fan beam 22. The cross-section of the truncated fan beam 22 depends in part on the cross-section of the slit 21 and the distance between the plate 20 and that point of the source 10 from which the energy is emitted. The fan beam 22 impinges on a rotating plate 30. The plate 30 has a number of slits 31 therein. As the fan beam 22 impinges on a portion of the plate 30 including a slit 31, a pencil beam 33 is emitted, and as the plate 30 rotates in the direction 32, the pencil beam scans in a generally downward direction. When the pencil beam 32 reaches the lowest point of intersection between the slit 31 and the fan beam 22, the pencil beam is inhibited by the opaque portions of the plate 30. However, at or shortly after this time, the upper portion of the fan beam 22 intercepts a subsequent slit 31 so that the pencil beam 33 again begins scanning in the downward direction. The pencil beam is directed at a region through which an object 60 supported on a conveyor 50 will more. This motion of the object 60 past the source of the pencil beam 33 results in a raster scanning action of the object 60 by the pencil beam 33. Those skilled in the art will understand that motion of the object 60 is not essential, what is necessary is relative motion between the object 60 and the scanning pencil beam 33, and that relative motion can be alternatively produced by motion of the source of the pencil beam 33.

The foregoing description is typical of the flying spot scanner as described in the Stein et al publication and patent. The present invention differs from that subject matter in accordance with the following description. The energy level of the source 10 is selected of a level sufficient to excite a selected fluorescence radiation line from targeted components which may lie within the object 60. At those times, when the pencil beam 33 intercepts portions of the object 60 whithin which targeted components exist, the interaction of the penetrating radiant energy and the targeted components with produce the selected fluorescent radiation line. The targeted component has been selected so that the selected fluorescent radiation line has sufficient energy to escape the object 60. As is apparent to those skilled in the art, this energy will be emitted in all possible directions. Radiation detectors 41 and 42 (sometimes referred to as a radiation detector 40) are positioned relative to the target 60 so that at least some of the selected fluorescent radiation line energy will impact on the detector 40. The detector 40 is fashioned as described below so that it will respond only or substantially only to this predetermined fluorescent radiation line and produce a corresponding electrical signal. This electrical signal can be employed to generate a shadowgraph type image. The shadowgraph type image will be different from either a projection radiograph image or a typical scatter shadowgraph image in that it will only illustrate the size, shape and position of the targeted components which respond to the illuminating energy of the pencil beam 33 by emitting the predetermined fluorescent radiation line. The video display hardware 70, as is apparent to those skilled in the art, is capable of responding to the fluorescence based signals from the detector 40 to produce the image which has just been referred to.

Figure 2:
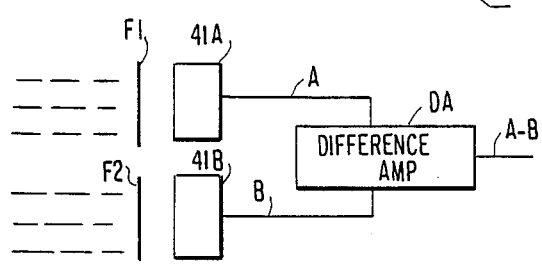
FIG. 2 schematically illustrates an arrangement for tailoring the response characteristics of a detector element 41 to a preselected fluorescent radiation line.
Figure 3:
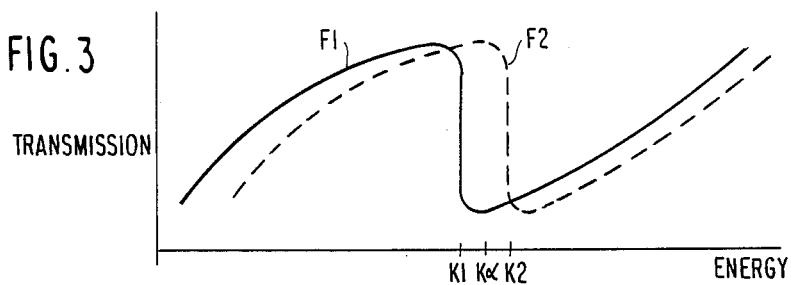
FIGS. 3 and 4 are curves useful in explaining the operation of FIG. 2.
Figure 4:
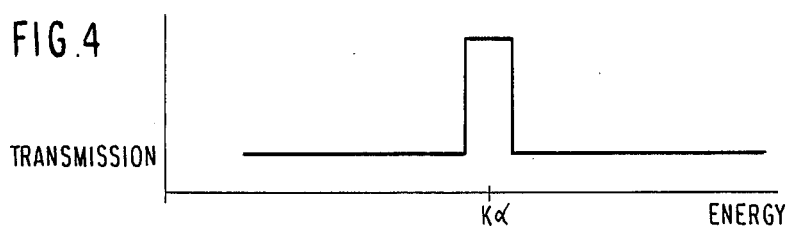

FIG. 2 shows an arrangement for tailoring the response of the detector 40 so that it responds substantially only to the predetermined fluorescent radiation line. FIGS. 3 and 4 show how the characteristic of the detector, including filters F1 and F2, restricts the response of the detector 41 to the predetermined fluorescent radiation line. More particularly, FIG. 3 (labelled transmission) shows the transmission characteristics of the filter elements F1 and F2, respectively. The thickness of the filter F1 is selected so there is a significant difference in attenuation (or transmission) across the K-edge, $K_1$. The second filter F2 is selected (in material and thickness) to have a nearly identical characteristic except that the K-edge, $K_2$, occurs at a higher energy level. The discontinuity in these transmission characteristics is a result of a particular K-edge. FIG. 3 also shows the location of the predetermined fluorescent radiation line $K_\alpha$. FIG. 4 (labelled $\Delta$ transmission) shows the energy characteristic passing the composite detector including filters F1 and F2. As shown in FIG. 4, the energy characteristic is relatively flat until an energy approximately equal to the K-edge discontinuity $K_1$ in the transmission characteristic of element F1. At this point, the transmission of the detector quickly rises, and it maintains this particular transmission characteristic as energy increases until an energy level is reached which is above $K_\alpha$, corresponding to the K-edge discontinuity $K_2$ in the characteristic of filter element F2. Above this energy level, the transmission characteristic of the detector is substantially the lower level exhibited for energies below the K-edge associated with the filter element F1. Since each element is reasonably transparent to its own fluorescent radiation, the filter F1 can comprise material identical to the targeted component. The second filter F2 comprises a material of higher Z and a nearly identical transmission characteristic except near the K-edge. Thus it should be apparent that by properly selecting the filters F1 and F2, the only energy passing detector 41 will be in the region of $K_\alpha$, the preselected fluorescent radiation line.

FIG. 2 shows an arrangement for achieving the characteristic such as that shown in FIG. 4. As shown in FIG. 2, the detector 41 is split into two detector elements 41A and 41B, both located so as to detect the scattered energy 61. A first filter element F1 is located between a source of the predetermined fluorescent radiation line and the detector element 41A, and a different filter element F2 is located between a different detector element 41B and the source of the predetermined fluorescent radiation line. Each of these detector elements develops a signal corresponding to the intensity of the energy inpinging on the detector. The signal A produced from the element 41A reflects the energy passing the filter element F1 and the signal B reflects the energy passing the filter element F2. A difference amplifier DA produces, at an output, the difference (A−B). It should be apparent to those skilled in the art that the arrangement of FIG. 2 produces an output signal (A−B) which, as a function of energy level, has the characteristic shown in FIG. 4. Thus the output (A−B) is the output of the detector 41. Of course, a similar arrangement is employed for other detectors (such as detector 42).

In the example which has already been referred to, the targeted component could be lead azide or mercury fulminate representing an explosive detonator, and if the object 60 include one or more such devices they would be outlined in the fluorescence based image produced by the hardware 70. A lead azide detonator can be expected to produce a fluorescent radiation line at either 75.0 or 85.0 kilovolts. On the other hand, a mercury fulminate detonator can be expected to exhibit fluorescence at 70.8 kilovolts or 80.2 kilovolts. Those skilled in the art should be aware that there are a wide variety of detectors which will response in this range, e.g. 70.8 to 85 kilovolts. On the other hand, using existing technology, such as a germanium lithium drifted detector or a silicon lithium drifted detector, the response of the detector 40 can be arranged to response within this range. For example, such detectors provide an electrical pulse whose height is related to the energy of the impinging photon. Using a pulse height analyzer, whose windows are programmable, the detector response can be rapidly tailored within the desired range. Nevertheless, for the purpose of this application, one example of a predetermined fluorescent radiation line can be considered to lie within the range of 70.8 to 85 kilovolts.

Those skilled in the art will readily recognize from the foregoing description and the description contained in our copending application referred to above that the apparatus shown in FIG. 1, in every case other than the detector 40, duplicates apparatus already present in the systems described in our copending application. Accordingly, the systems described in our copending application can be enhanced by adding the detector 40 and using the signals produced thereby in a number of ways. Inasmuch as the fluorescent energy is radiated in all directions, the position of detector 40 is relatively arbitrary and it can be placed so as to avoid interfering with the location of the backscatter detector 25A, 25B of our copending application.

The signals produced by the detector 40 in a system such as any of the systems shown in our copending application can be used in a number of ways. In one arrangement, a video display and associated hardware is employed to respond to signals from the detector 40 so as to develop a fluorescence based image in addition to the other two (or three) images produced by the other apparatus described in our copending application.

Because the signals produced by the detector 40 will be synchronous with signals produced by the other detectors, the signals produced by the detector 40 can be used to highlight images produced by any of the detectors shown in the apparatus of our copending application. Accordingly, in addition to or in lieu of the fluorescence based image, we can highlight the transmitted image, or the forward or back scatter image produced by the apparatus described in our copending application.

Figure 5:
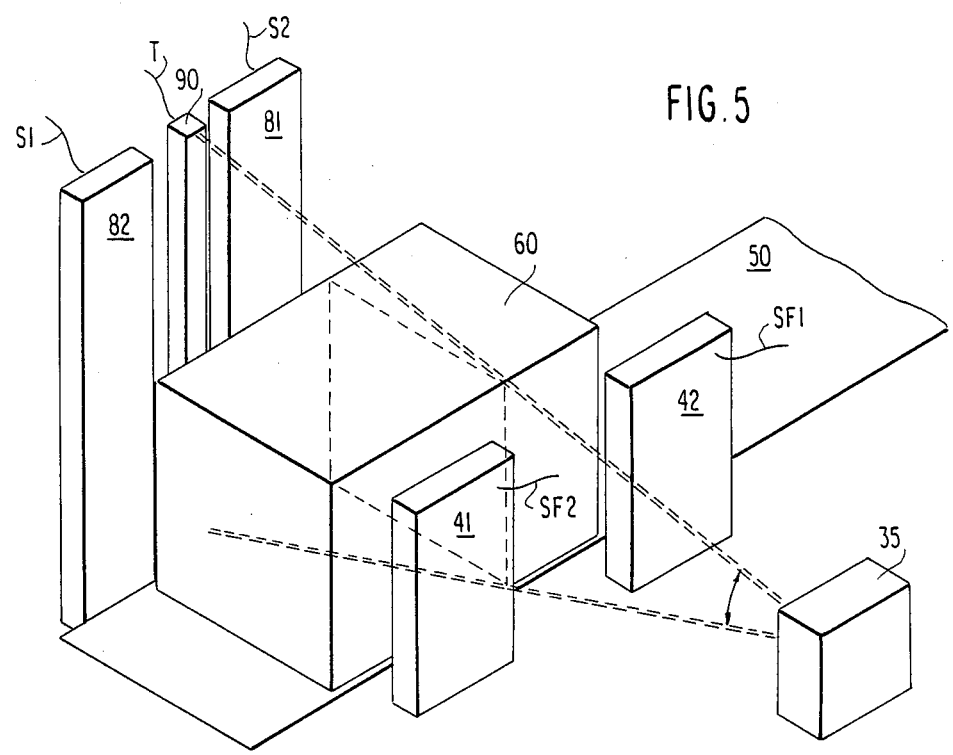
FIG. 5 illustrates a different embodiment of the invention which employs a transmit energy detector 90, a scatter detector 80 (comprising scatter detecting elements 81 and 82) and a fluorescence detector 40 (comprising fluorescent detector elements 41 and 42)
Figure 6:
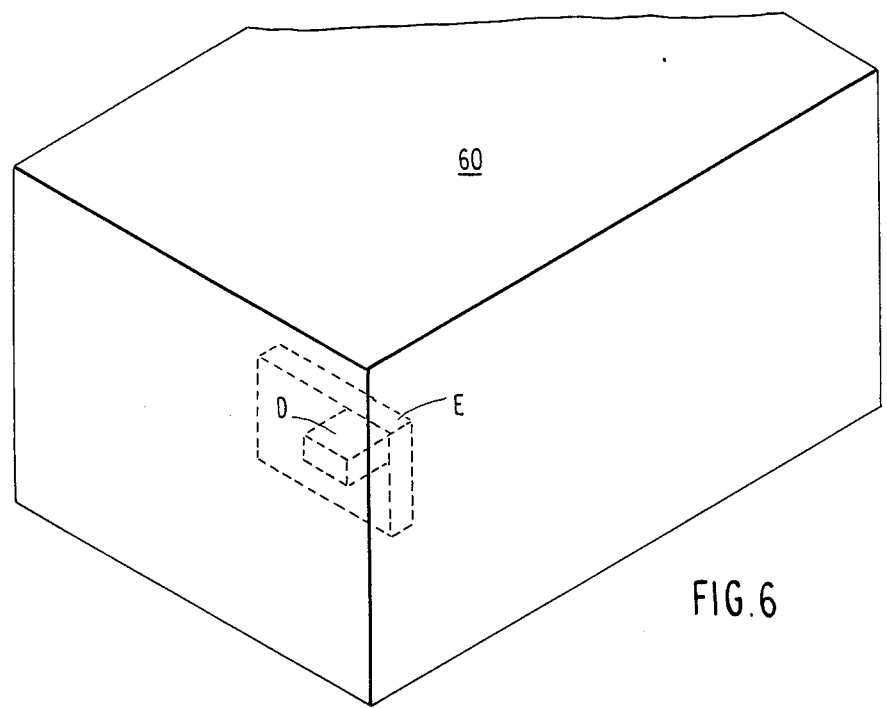
FIG. 6 shows an object to be imaged in accordance with one example, which object includes a detonator component D and an explosive component E.

In addition to or in lieu of all of the foregoing alternatives, the signals produced by the detector 40 can be coupled to energize an alarm (audible, visual, tactile or otherwise) when the amplitude of the signals produced by the detector 40 exceed a predetermined threshold. FIG. 5 is an example of one embodiment of the invention. FIG. 5 shows that a source of penetrating radiation including a flying spot scanner, represented at 35 (which may include the elements 10, 11, 20, 21, 22, 30 and 31 of FIG. 1), illuminates an object 60 which is carried past the scanner 35 on a conveyor 50. A plurality of detectors are provided for detecting different forms of energy resulting from this illumination. A transmit energy detector 90 is located on the other side of the object 60 relative to the source 35. The flying spot scans a line in space which is occupied by the detector 90. The detector 90 produces electrical signals reference T. A scatter detector 80, comprising scatter detecting elements 81 and 82 are also provided located adjacent the transmit energy detector 90. The scattered energy detector 80 produces signals on the lines S1 and S2. The signals on these lines are added to produce a single output referenced S1, S2. In addition, in accordance with the invention, the added detector 40 is provided for detecting a preselected fluorescent radiation line; detector 40 comprises detector elements 41 and 42 which are arranged to response substantially only to the preselected fluorescent radiation line as described for example in FIGS. 2 and 3. The detector elements 41, 42 produce electrical signals on the lines SF1 and SF2, respectively. The signals on these lines are summed to produce a signal output referenced SF1, SF2. For purposes of discussion, we assume that FIG. 6 shows that internal to the target 60 are located a detonator D in close proximity to an explosive E. For purposes of this description, we will assume that as is typical of explosives, the explosive E consists of an element or compound with low atomic number $Z_E$. On the other hand, the detonator D may comprise mercury fulminate which has an element or compound of relatively high atomic number $Z_D$. The energy of the source 35 is selected in energy level sufficient to excite the preselected fluorescent radiation line corresponding to $Z_D$, and the detector 40 is arranged to respond to this predetermined fluorescent radiation line.

In accordance with one embodiment of the invention, FIG. 7 shows a trio of displays, a transmit display TD, a scatter display SD and a fluorescence display FD. The displays are driven from electronic equipment which is responsive to the outputs from the detectors 40, 80 and 90. As shown in FIG. 7, the output of the transmit detector 90T is the signal input to TD, the output of the scatter detector 80, S1, S2 is the signal input to SD, and the output of the fluorescent detector 40, SF1, SF2 is the signal input to FD. Furthermore, an audible alarm A is driven by the signals SF1, SF2. If desired, the audible alarm A has a threshold device TH, such that only when the input signal SF1, SF2 is above a predetermined threshold, is the alarm A sounded. Based on the foregoing discussion it should by now be apparent that the display TD will show the detonator D and to a lesser extent the explosive E, the display SD will illustrate the explosive E, and the display FD will illustrate the detonator D. An operator viewing this trio of displays mentally associates the position on the display of the detonator D and the explosive E to assit in readily identifying the presence of a bomb. The audible alarm A serves to call the operator's attention to the presence somewhere in the object 60 of a material emitting the preselected fluorescent radiation line indicative of the detonator D.

In an alternative embodiment of the invention, the display SD and its inputs remain as in the embodiment shown in FIG. 7. However, the input to the display TD is altered. The signal T is subjected to a first gain G1, and the fluorescent signal SF1, SF2 is subjected to a different preselected gain G2. The signals are then summed and provided as the signal input to the display TD. From the foregoing, it will be appreciated that not only will the display TD show the position of the detonator D, but that component in any image will be highlighted, identifying it is an object emitting the preselected fluorescent radiation line.

In a further embodiment of the invention shown in FIG. 9, the signal input and the resulting image on the display TD is the same as it was in the embodiment of FIG. 7. However, the signal input and the resulting image on the display SD is changed. More particularly, the scatter signal S1, S2 is subjected to a predetermined gain G3 and the fluorescence signal SF1, SF2 is subjected to a gain G4. The signals, after the gain adjustment, are summed and provided as the signal input to the display SD. The resulting image on the display will show the explosive E (as was the case in FIGS. 7 and 8), but it will also show the detonator D.

It should be readily apparent from reviewing FIGS. 8 and 9 that an operator viewing these images can readily detect the potential presence of a bomb within the object 60.

As has already been described, the scatter and fluorescence radiation comes off from the object 60 throughout a 360° solid angle such that the scatter detectors and the fluorescence detector can be located anywhere which is convenient. FIG. 5 shows an arrangement in which the scatter detecting elements 81, 82 detect forward scatter, e.g. the scatter detector is located further from the source than the object, and the fluorescence detecting elements 41 and 42 are located closer to the source than the object. However, it is within the scope of the invention to interchange the locations of these detectors so the scatter detector comprises a backscatter detector, e.g. located closer to the source than the object and the fluorescence based detectors are further from the source than the object. Other, unillustrated embodiments of the invention would include locating either the scatter detector and/or the fluorescence detector in the unoccupied region above the object being illuminated. It is also within the scope of the invention to include scatter detecting elements and fluorescence detecting elements either closer to the object than the source or further from the object and the source. To optimize the response of the scatter and fluorescence based detectors, the solid angle subtended by the detectors relative to the source of scattered or fluorescent radiation is maximized. There are of course physical constraints on the location and active areas of the detectors inasmuch as not detector can be located in the path of the object and only a single detector can occupy any location at any time. However, within these constraints, the scatter and fluorescence detector' locations can be widely varied.

It should be apparent that the invention is not limited to the preceding particularly described examples. In general, the radiation signature of a particular object or class of objects sought to be detected is analyzed in terms of production of transmit based signals, scatter based signals and fluorescence based signals. Detectors are then selected and positioned so as to collect and discriminate on energy selected to both detect the pressure of such a targeted component as well as to distinguish its presence from other components which have different radiation signatures. Application of the invention reduces the burden placed on the operator to distinguish targeted components from the mass of other, irrelevant components which typically clutter the displays associated with equipment low now in use.

Having thus described our invention, what we claim as new, and desire to secure by Letters Patent is:

1. Apparatus useful in imaging for inspecting objects to highlight targeted components of selected radiation signature comprising:
    (a) a source of penetrating radiation selected to object,
    (b) means for repeatedly scanning a pencil beam of radiation, from said source along a line in space,
    (c) means providing relative motion between said object to be imaged and said line in space,
    (d) first radiation energy detector means located to be responsive to radiant energy penetrating said object and emerging from said object, substantially unchanged in direction, for producing first electrical signals,
    (e) second radiant energy detector means responsive to a predetermined fluorescent radiation line emitted from said targeted components of said object for generating second electrical signals,
    (f) display means responsive to said first electrical signals for producing a shadowgraph image of said object, and
    (g) first means responsive to said second electrical signals for generating an indication of presence of said predetermined fluorescent radiation line.

2. The apparatus of claim 1 in which said first means includes means to highlight those portions of said shadowgraph image identified by said second electrical signals.

3. The apparatus of claim 1 in which said first means includes means for producing a shadowgraph image in response to said second electrical signals.

4. The apparatus of claim 33 in which said first means includes an alarm means energized in response to said second electrical signals for generating an alarm signal.

5. Apparatus useful in imaging for inspecting objects to highlight targeted components of selected radiation signatures comprising:
    (a) a source of penetrating radiation selected to produce fluorescence from targeted components of said object,
    (b) means for forming radiation emitted by said source into a beam of predetermined cross-section and for repeatedly sweeping said beam across a line in space,
    (c) means providing relative motion between said object to be imaged and said line in space,
    (d) radiation detector means responsive to a predetermined fluorescent radiation line emitted from said targeted components of said object for generating fluorescence electrical signals, and
    (e) display means responsive to said electrical signals to develop a shadowgraph image of said targeted components of said object emitted said fluorescent radiation line, which further includes:
    scatter detector means responsive to radiation emitted from said object scattered in direction from said source for generating scatter signals, and
    scatter display means responsive to said scatter signals for generating a scatter image of said object.

6. Apparatus as recited in claim 5 in which said scatter display means includes means responsive to said fluorescence electrical signals for highlighting selected portions of said scatter image.

7. Apparatus as recited in claim 6 in which said scatter detector means is located further from said source than said object.

8. Apparatus as recited in claim 6 in which said scatter detector means is located closer to said source than said object.

9. Apparatus as recited in any one of claims 5-8 which further includes alarm means responsive to said fluorescence electrical signals for generating an alarm signal.

10. Apparatus useful in imaging for inspecting objects to highlight targeted components of selected radiation signatures comprising:
   (a) a source of penetrating radiation selected to produce fluorescence from targeted components of said object,
   (b) means for repeatedly scanning a pencil beam of radiation, from said source along a line in space,
   (c) means providing relative motion between said object to be imaged and said line in space,
   (d) radiation detector means responsive to radiation emitted from said object for generating first electrical signals,
   (e) second radiation detector means responsive to a predetermined fluorescent radiation line emitted from said targeted components of said object for generating second electrical signals,
   (f) display means responsive to said first electrical signals to develop a shadowgraph image of said object, and
   (g) means for highlighting portions of said shadowgraph image in response to said second electrical signals.

11. Apparatus as recited in claim 10 in which:
said radiation detector means comprises scatter detector means responsive to radiatio emitted from said object scattered in direction from said source for generating scatter signals, and said display means comprises scatter display means responsive to said scatter signals for generating a scatter image of said object.

12. Apparatus as recited in claim 11 in which said scatter detector means is located further from said source than said object.

13. Apparatus as recited in claim 11 in which said scatter detector means is located closer to said source than said object.

14. Apparatus as recited in claim 10 in which:
said radiation detector means comprises transmission detector means responsive to radiation emitted from said object unchanged in direction from said source for generating transmission signals, and said display means comprises transmission display means responsive to said transmission signals for generating a transmission image of said object.

15. Apparatus as recited in claim 14 which further includes:
scatter detector means responsive to radiation emitted from said object scattered in direction from said source for generating scatter signals, and scatter display means responsive to said scatter signals for generating a scatter image of said object.

16. Apparatus as recited in any one of claims 10-15 which further includes alarm means responsive to said second electrical signals for generating an alarm signal.

17. Apparatus useful in imaging for inspecting objects to highlight targeted components of selected radiation signatures comprising:
   (a) a source of penetrating radiation selected to produce fluorescence from targeted components of said object,
   (b) means for repeatedly scanning a pencil beam of radiation, from said source along a line in space,
   (c) means providing relative motion between said object to be imaged and said line in space,
   (d) radiation detector means responsive to radiation emitted from said object for generating first electrical signals,
   (e) second radiation detector means responsive to a predetermined fluorescent radiation line emitted from said targeted components of said object for generating second electrical signals,
   (f) display means responsive to said first electrical signals to develop a shadowgraph image of said object, and
   (g) alarm means for alerting an operator in response to said second electrical signals.

18. Apparatus as recited in claim 17 in which:
said radiation detector means comprises transmission detector means responsive to radiation emitted from said object unchanged in direction from said source.

19. Apparatus as recited in claim 18 in which said display means includes means responsive to said second electrical signals for highlighting portions of an image developed on said display means.

20. Apparatus as recited in claim 17 in which:
said radiation detector means comprises scatter detector means responsive to radiation emitted from said object scattered in direction from said source.

21. Apparatus as recited in claim 20 in which said scatter detector means is located further from said source than said object.

22. Apparatus as recited in claim 20 in which said scatter detector means is located closer to said source than said object.

23. Apparatus useful in imaging for inspecting objects to highlight components of selected radiation responsive signatures comprising:
   (a) a source of penetrating radiation selected to produce fluorescence from targeted components of said object,
   (b) means for repeatedly scanning a pencil beam of radiation, from said source along a line in space,
   (c) means providing relative motion between said object to be imaged and said line in space,
   (d) first radiation energy detector means located to be responsive to radiation energy penetrating said object and emerging from said object, substantially unchanged in direction, for producing first electrical signals,
   (e) second radiant energy detector means responsive to radiant energy scattered by said object for producing second electrical signals,
   (f) third radiant energy detector means responsive to a predetermined fluorescent radiation line emitted from said targeted components of said object for generating third electrical signals.

24. Apparatus as recited in claim 23 which further includes display means responsive to said first electrical signals for producing a transmission image of said object.

25. Apparatus as recited in claim 24 in which said display means includes means responsive to said third electrical signals for highlighting portions of said transmission image.

26. Apparatus as recited in claim 24 which further includes alarm means responsive to said third electrical signals for producing an alarm signal.

27. Apparatus as recited in claim 26 which further includes scatter display means responsive to said second electrical signals for producing a scatter image of said object.

28. Apparatus as recited in claim 27 in which said second radiant energy detector means is located further from said source than said object.

29. Apparatus as recited in claim 27 in which said second radiant energy detector means is located closer to said source than said object.

30. Apparatus as recited in claim 23 which further includes display means responsive to said second electrical signals for producing a scatter image of said object.

31. Apparatus as recited in claim 30 in which said display means includes means responsive to said third electrical signals for highlighting portions of said scatter image.

32. Apparatus as recited in claim 31 which further includes alarm means responsive to said third electrical signals for producing an alarm signal.

33. Apparatus useful in imaging for inspecting objects to highlight targeted components of selected radiation signatures comprising:
   (a) a source of penetrating radiation selected to produce fluorescence from targeted components of said object,
   (b) means for forming radiation emitted by said source into a beam of predetermined cross-section and for repeatedly sweeping said beam across a line in space,
   (c) means providing relative motion between said object to be imaged and said line in space,
   (d) radiation detector means responsive to a predetermined fluorescent radiation line emitted from said targeted components of said object for generating fluorescence electrical signals, and
   (e) display means responsive to said electrical signals to develop a shadowgraph image of said targeted components of said object emitting said fluorescent radiation line, which further includes:
   transmission detector means responsive to radiation emitted from said object unchanged in direction from said source for generating transmission signals, and
   transmission display means responsive to said transmission signals for generating a transmission image of said object.

34. Apparatus as recited in claim 33 in which said transmission display means includes means responsive to said fluorescence electrical signals for highlighting selected portions of said transmission image.

35. Apparatus as recited in claim 33 or claim 34 which further includes alarm means responsive to said fluorescence electrical signals for generating an alarm signal.

36. Apparatus useful in imaging for inspecting objects to highlight components of selected radiation responsive signatures comprising:
   (a) a source of penetrating radiation selected to produce fluorescence from targeted components of said object,
   (b) means for repeatedly scanning a pencil beam of radiation, from said source along a line in space,
   (c) means providing relative motion between said object to be imaged and said line in space,
   (d) first radiation energy detector means for producing first electrical signals, located to be responsive to radiation energy penetrating said object and emitted from said object, and
   (e) radiation detector means responsive to a predetermined fluorescent radiation line emitted from targeted components of said object for generating second electrical signals.

37. Apparatus as recited in any one of claims 37–43 which further includes alarm means responsive to said second electrical signals for producing an alarm.

38. Apparatus as recited in claim 37 in which:
   said apparatus further includes display means responsive to said first electrical signals for producing a shadowgraph image.

39. Apparatus as recited in claim 38 in which: said first radiant energy detector means comprises transmission detector means responsive to radiant energy emitted from said object unchanged in direction from said source.

40. Apparatus as recited in claim 38 in which: said first radiant energy detector means comprises scatter detector means responsive to radiant energy scattered in direction from said source by said object.

41. Apparatus as recited in claim 40 in which said scatter detector means is located further from said source than said object.

42. Apparatus as recited in claim 40 in which said scatter detector means is located closer to said source than said object.

43. Apparatus as recited in claim 38 in which said display means includes means responsive to said second electrical signals for highlighting those portions of said image identified by said second electrical signals.

* * * * *